(12) United States Patent
Lee et al.

(10) Patent No.: US 10,406,230 B2
(45) Date of Patent: Sep. 10, 2019

(54) EXENDIN-4 ANALOGUE PEGYLATED WITH POLYETHYLENE GLYCOL OR DERIVATIVE THEREOF, PREPARATION METHOD THEREOF, AND PHARMACEUTICAL COMPOSITION FOR PREVENTING OR TREATING DIABETES, CONTAINING SAME AS ACTIVE INGREDIENT

(71) Applicant: D&D Pharmatech Inc., Seongnam-Si, Gyeonggi-Do (KR)

(72) Inventors: Sung Kwon Lee, Seoul (KR); Won Bae Kim, Seoul (KR); Seulki Lee, Eldridge, MD (US); Tae Hyung Kim, Goyang-si (KR)

(73) Assignee: D&D Pharmatech Inc., Seongnam-si (KR)

( * ) Notice: Subject to any disclaimer, the term of this patent is extended or adjusted under 35 U.S.C. 154(b) by 62 days.

(21) Appl. No.: 15/413,029

(22) Filed: Jan. 23, 2017

(65) Prior Publication Data
US 2017/0189545 A1 Jul. 6, 2017

Related U.S. Application Data

(63) Continuation of application No. 13/882,361, filed as application No. PCT/KR2012/005137 on Jun. 28, 2012, now abandoned.

(30) Foreign Application Priority Data

Jun. 28, 2011 (KR) ........................ 10-2011-0062858

(51) Int. Cl.
| | | |
|---|---|---|
| *C07K 14/575* | (2006.01) |
| *A61K 38/22* | (2006.01) |
| *A61K 47/02* | (2006.01) |
| *A61K 47/60* | (2017.01) |
| *A61K 9/00* | (2006.01) |
| *A61K 47/26* | (2006.01) |
| *A61K 9/20* | (2006.01) |
| *A61K 9/48* | (2006.01) |

(52) U.S. Cl.
CPC ............ *A61K 47/02* (2013.01); *A61K 9/0019* (2013.01); *A61K 9/2018* (2013.01); *A61K 9/2059* (2013.01); *A61K 9/4858* (2013.01); *A61K 9/4866* (2013.01); *A61K 38/2278* (2013.01); *A61K 47/26* (2013.01); *A61K 47/60* (2017.08); *C07K 14/57563* (2013.01)

(58) Field of Classification Search
CPC .......... A61K 38/2278; A61K 47/48215; C07K 14/57563
See application file for complete search history.

(56) References Cited

U.S. PATENT DOCUMENTS

| | | |
|---|---|---|
| 2006/0286066 A1 | 12/2006 | Basran |
| 2012/0196795 A1 | 8/2012 | Xu |

FOREIGN PATENT DOCUMENTS

| | | |
|---|---|---|
| KR | 1020020001719 | 1/2002 |
| KR | 1020070115602 | 6/2007 |
| KR | 1020110007362 | 1/2011 |
| WO | 200069911 | 11/2000 |
| WO | 2004022004 | 3/2004 |
| WO | 2006042848 | 4/2006 |
| WO | 2007075534 | 7/2007 |
| WO | 2008130066 | 10/2008 |
| WO | 2010121559 | 10/2010 |

OTHER PUBLICATIONS

Berendsen, "A glimpae of the holy grail", Science 282:642-3 (1998).
Bradley, et al., Limits of cooperativity in a structurally modular protein: Response of the motch ankyrin domain to analogous alanine substitutions im each repeat, J Mol Biol, 324:373-86 (2002).
Davidson, "Advances in therapy for type 2 GLP-1 receptor agonists and DPP-4 inhibitors", Cleveland Clinic J Med., 76: Supp 5 (2009).
Definitiom of of Analogue amd Dericitice, On-line medical Dictionary, accessed Mar. 5, 2000.
Definition of Dimer, thefreedictionary.com. 2 pages, accessed Dec. 8, 2014.
Definition of Trimer, thefreedictionary.com, 2 pages, accessed Dec. 8, 2014.
Diabetes, Diabetes sympotoins, The Mayo Clinic,https://www.mayoclinic.org/diseases-conditions/diabetex/in-depth/diabetes-symptoms/art, accessed Dec. 9, 2014.
European Search Report for EP 12804683 dated Nov. 20, 2014.
Gong, et al., "Research paper: Site-specific PeGylation of exenatide analogues markedly improved their glucoregulatory activity", British J Pharma., 399-412 (2011).
Kim, et al., "Mono-PEGylated dimeric exendin-4 as high receptor binding and long-acting conjugatrs for type 2 anti-diabetes therapeutics", Bioconjugate Chem., 625-32 (2011).
Kim, et al., "Mono-PEGylated dimeric exendin-4 as high receptor binding and long-acting conjugates for type 2 anti-diabetes therapeutics", Bioconjug Chem., 22(4):625-32 (2011).

(Continued)

*Primary Examiner* — James H Alstrum-Acevedo
*Assistant Examiner* — Erinne R Dabkowski
(74) *Attorney, Agent, or Firm* — Pabst Patent Group LLP

(57) ABSTRACT

The present disclosure relates to an exendin-4 analog PEGylated with polyethylene glycol or a derivative thereof, a preparation method, and a pharmaceutical composition for prevention or treatment of diabetes containing the same as an active ingredient. According to the present invention, the yield of an exendin-4 analog can be increased via the selective PEGylation by using exendin-4 in which a cysteine is introduced into #40 site of the C-terminal, and treatment effect of medications can be increased, so that the exendin-4 analog can be usefully applied as a composition for prevention or treatment of diseases caused by insulin hypersecretion.

20 Claims, 12 Drawing Sheets
Specification includes a Sequence Listing.

(56) References Cited

OTHER PUBLICATIONS

Kim, et al., "Site-specific PEGylated Exendin-4 modified with a high molecular weight trimeric PEG reduces steric hindrance and increases type 2 antidiabetic therapeutic effects", Bioconjug Chem., 23(11):2214-20 (2012).
Ngo, et al., "Computational complexity", Protein Structure Protection and the Lecinthal Paradox, pp. 491-494 (1994).
Rudinger, "Peptide Hormones", JA Parsons, Ed pp. 1-7 (1976).
Sigma, "Design custom peptides", Sigma and Genosys, pp. 1-2 (2004).
Taimr, et al., "Activated stellate cells express the TRAIL receptor-2/death receptor-5 and undergo TRAIL-mediated apoptosis", Hepatology, 37(1):87-95 (2003).
Voet, "Abnormal hemoglobins", Biochemistry, John Wiley and Sons inc., Second Edition, pp. 235-241 (1995).
Xue, "Exendin-4 treatments of nonobase diabetic mice increases beta-cell proliferation and fractional insulin reactive area", J Diabetes Compilc., 24:163-7 (2010).

SEQUENCE LISTING

```
<160> NUMBER OF SEQ ID NOS: 2

<210> SEQ ID NO 1
<211> LENGTH: 40
<212> TYPE: PRT
<213> ORGANISM: Artificial Sequence
<220> FEATURE:
<223> OTHER INFORMATION: Peptide

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Cys
        35                  40

<210> SEQ ID NO 2
<211> LENGTH: 39
<212> TYPE: PRT
<213> ORGANISM: Artificial Sequence
<220> FEATURE:
<223> OTHER INFORMATION: Peptide

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

EXENDIN-4 ANALOGUE PEGYLATED WITH POLYETHYLENE GLYCOL OR DERIVATIVE THEREOF, PREPARATION METHOD THEREOF, AND PHARMACEUTICAL COMPOSITION FOR PREVENTING OR TREATING DIABETES, CONTAINING SAME AS ACTIVE INGREDIENT

CROSS-REFERENCE TO RELATED APPLICATIONS

This application is a continuation of pending U.S. application Ser. No. 13/882,361, filed Apr. 29, 2013, which is a 371 application of International Application No. PCT/KR2012/005137, filed Jun. 28, 2012, which claims priority to and benefit of Korean Patent Application No. 10-2011-0062858, filed Jun. 28, 2011, the disclosures of which are hereby incorporated herein by reference in their entirety.

TECHNICAL FIELD

The present disclosure relates to an exendin-4 analogue PEGylated with polyethylene glycol or a derivative thereof, a preparation method thereof, and a pharmaceutical composition for prevention or treatment of diabetes containing the same as an active ingredient.

REFERENCE TO SEQUENCE LISTING

The Sequence Listing submitted Aug. 21, 2014, as a text file named "THER_103_ST25.txt," created on Apr. 9, 2014, and having a size of 1,374 bytes is hereby incorporated by reference.

BACKGROUND ART

Among pharmaceutical technologies, PEGylation of peptides and proteins for the purpose of treatment is the most effective technology. PEGylation of peptides and proteins increases molecular weight thereof, protein degradation site defense and immunogenicity site defense, which consequently increases half-life of in vivo medications and reduce immunogenicity of peptides and proteins. Therefore, PEGylation technology has an effect of increasing treatment effect by solving problems of original medications, and due to such strength, serves an important role in increasing effects of PEGylated peptide and protein medication delivery system.

Also, peptides and proteins increase treatment effect by covalently bonding with polyethylene glycol (PEG). Such technology increases molecular weight, defense of a metabolism site and inhibition of an immunogenicity site, increasing in vivo half-life and stability and reducing immunogenicity. Furthermore, kidney excretion of peptides and proteins bound with PEG is reduced due to the increase of molecular weights of peptides and proteins by PEG, so that PEGylation has advantages of increasing effects in both pharmacokinetically and pharmacodynamically.

PEGylation reacting sites of peptides and proteins are randomly dispersed and are occasionally close to bioactive sites. However, traditional PEGylation employs nonspecific PEGylation methods that do not consider PEG reacting site, number of PEG bonds and biological activity. However, such a nonspecific PEGylation method reduces treatment effects by bringing insufficient conformation by producing various branched type PEG-bonded isomers that have different physiochemical, biological and pharmacokinetic characteristics. Specific PEGylation methods have been studied to solve such problems, and recently the specific PEGylation methods are rapidly developing to become a method of maximizing medications' treatment effects as genetic engineering technology and selective functional group introducing technology are quickly developing. In a related art, a study of selectively binding PEG into N-terminal site after removing a reaction site by substituting primary amine site with different amino acid using genetic engineering method for granulocyte stimulating factor (G-CSF) and tumor necrosis factor receptor has been conducted previously.

Also, studies using a technology that selectively PEGylates substituent after having introduced a specific substituent using genetic engineering methods and substitution technology for medications such as staphylokinase, interferon a-2, antibody single chain fragment variable (ScFv), have been conducted.

Exendin-4 is a polypeptide substance and is the first incretin analogue, a diabetes medication prepared by synthesizing exendin-4, a salivary substance of Gila monster. Exendin-4 is different from exendin-3 for only #2 and #3 sites, is known to have a longer half-life than glucagon like peptide-1 (GLP-1) which is a diabetes medication having a half-life shorter than two minutes for DPP-IV, an enzyme that is resistant for directly degrading incretin enzyme that is produced in mammals' stomachs after ingestion by DPP-IV (dipeptidyl peptidase-4) to serve beneficial roles of promoting insulin secretion and lowering blood sugar level, and also, it shows 2-4 hours of half-life in vivo experiment, and it has been confirmed that it can reach enough blood concentration with 2-3 times of intraperitoneal injection per day.

Also, exendin-4 is known to control gastrointestinal tracts' motility, reduces food intake and suppresses blood plasma glucagon, and recently PLGA microsphere type synthetic exendin-4 (product name: Byetta) has been authorized by US FDA and is about to be released. However, since this Byetta LAR product has complicated preparation process and is short in vivo half-life for exendin-4, which is about 4-6 hours, frequent administration of high dose exendin-4 is required, and the problem of medication release control based on quick excretion due to the low molecular weight of lower than 4200, and problems such as immunogenicity still exist.

Therefore, while studying a method to reduce administration frequency of exendin-4 and solve the low molecular weight problem of exendin-4, the inventors have completed the present invention after having confirmed the fact that it is possible to increase the production yield of PEGylated exendin-4 and treatment effect of medications by performing selective PEGylation via insertion of cysteine (Cys) amino acid into the site (#40 site) next to #39 site of C-terminal of exendin-4.

DISCLOSURE OF THE INVENTION

Technical Problem

One object of the present invention is to provide an exendin-4 analogue in which a cysteine (Cys) is introduced into #40 site of C-terminal and is PEGylated with polyethylene glycol (PEG) or derivatives thereof.

Another object of the present invention is to provide a method of preparing the exendin-4 analogue.

Still another object of the present invention is to provide a pharmaceutical composition for prevention or treatment of diseases caused by insulin hypersecretion, containing the exendin-4 analogue as an active ingredient.

Technical Solution

In order to achieve the objects, the present invention provides an exendin-4 analogue that has a cysteine (Cys) introduced into #40 site of C-terminal, which is PEGylated with polyethylene glycol (PEG) or derivatives thereof.

The present invention also provides a method of preparing the exendin-4 analogue.

Furthermore, the present invention provides a pharmaceutical composition for prevention or treatment of diseases caused by insulin hypersecretion containing the exendin-4 analogue as an active ingredient.

Advantageous Effects

According to the present invention, by performing selective PEGylation, the yield of an exendin-4 analogue in which a cysteine (Cys) is introduced into #40 site of the C-terminal and is PEGylated with polyethylene glycol (PEG) or derivatives thereof, can be increased, and treatment effect of medications can be increased, and thus the exendin-4 analogue can be beneficially used as a composition for prevention or treatment of diseases caused by insulin hypersecretion.

MODE FOR CARRYING OUT THE INVENTION

Figure 1:
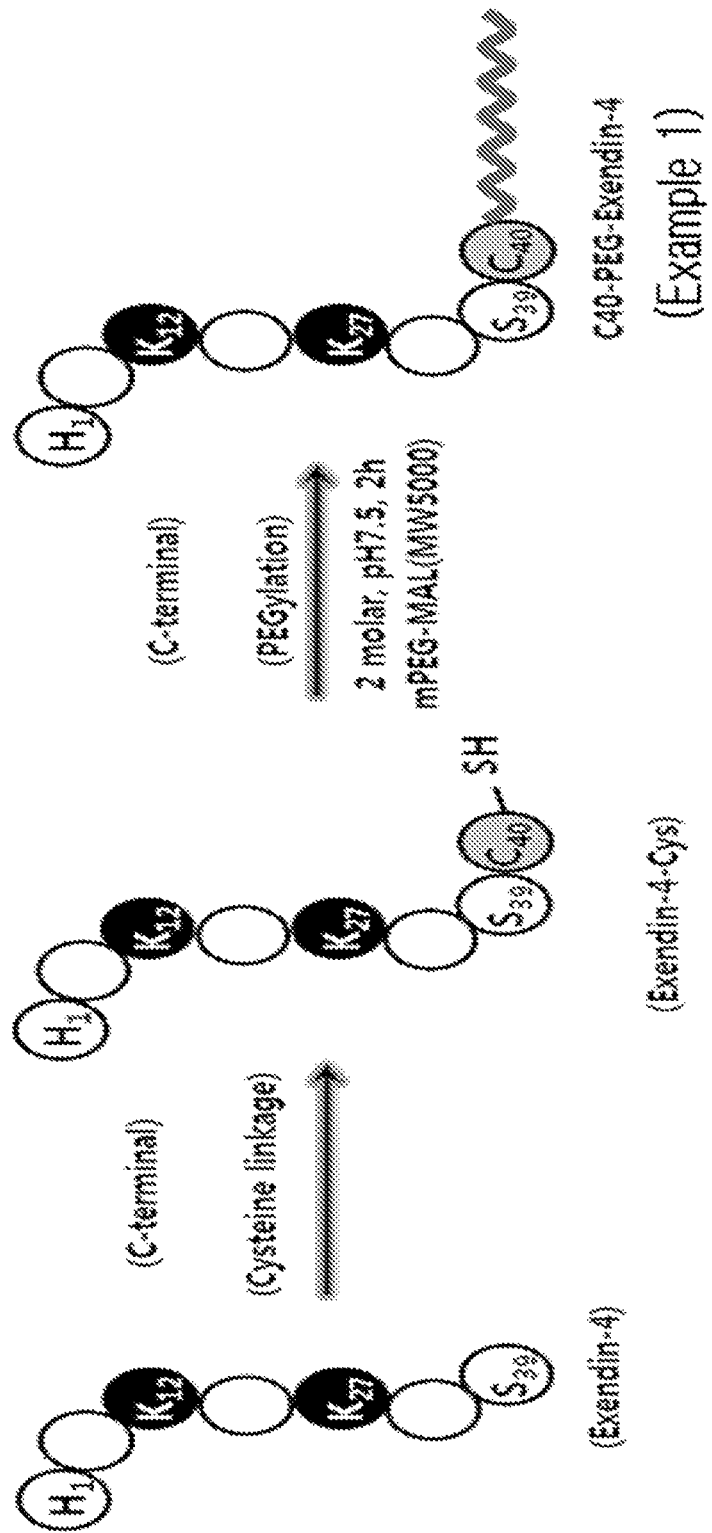
FIG. 1 is a schematic view illustrating PEGylation of exendin-4 in which cysteine (Cys 40) is introduced into the C-terminal of example 1 of the present invention.

Hereinafter, the present invention will be described in detail.

The present invention provides an exendin-4 analogue in which a cysteine (Cys) is introduced into #40 site of the C-terminal and is PEGylated with polyethylene glycol (PEG) or a derivative thereof.

The molecular weight of polyethylene glycol or a derivative thereof according to the present invention is 5-60 kDa, and preferably 20-50 kDa, but is not limited thereto.

Also, the polyethylene glycol or a derivative thereof according to the present invention is a linear type or a branched type, and for the branched type, preferably a dimeric type or a trimeric type may be used, and more preferably a trimeric type may be used.

Specifically, the polyethylene glycol derivative is, for example, methoxypolyethylene glycol succinimidylpropionate, methoxypolyethylene glycol N-hydroxysuccinimide, methoxypolyethylene glycol propionaldehyde, methoxypolyethylene glycol maleimide, or multiple branched types of these derivatives. Preferably, the polyethylene glycol derivative is linear methoxypolyethylene glycol maleimide, branch type methoxypolyethylene glycol maleimide or trimeric methoxypolyethylene glycol maleimide, and more preferably is trimeric methoxypolyethylene glycol maleimide.

Also, the present invention provides a method of preparing an exendin-4 analogue PEGylated with the polyethylene glycol or a derivative thereof, which includes a process of dissolving exendin-4 in which cysteine is introduced into #40 site of the C-terminal, and polyethylene glycol or a derivative thereof in phosphate buffer saline solution and reacting them at room temperature.

Specifically, an exendin-4 analogue PEGylated with polyethylene glycol or a derivative thereof may be prepared by adding exendin-4 in which cysteine is introduced into #40 site of the C-terminal, and polyethylene glycol or a derivative thereof in a phosphate buffer saline solution in a mole ratio of 1:1-3 in a phosphate buffer saline having a pH range of 7.2-7.8, preferably pH 7.5, dissolving these ingredients, and perform a reaction for 1-3 hours at room temperature although the reaction temperature is not particularly limited, and performing a column chromatography after the reaction is completed.

When the phosphate buffer saline is not within the pH range, the yield may decrease.

In the present invention, after the exendin-4 analogue PEGylated with polyethylene glycol or the derivative thereof is prepared, the molecular structure of the exendin-4 analogue may be confirmed by a mass spectroscope, a liquid chromatography, an X-ray diffraction analysis, a polarimetry, and comparison between calculated values and measured values of representative elements constituting the exendin-4 analogue.

Also, the present invention provides a pharmaceutical composition for prevention or treatment of diseases caused by insulin hypersecretion, containing the exendin-4 analogue as an active ingredient.

Furthermore, the present invention provides a treatment method characterized with administration of the exendin-4 analogue PEGylated with polyethylene glycol or a derivative thereof to patients in need of treating the diseases caused by insulin hypersecretion.

The diseases caused by insulin hypersecretion may include Type 1 diabetes, Type 2 diabetes and diabetes complications.

Figure 10:
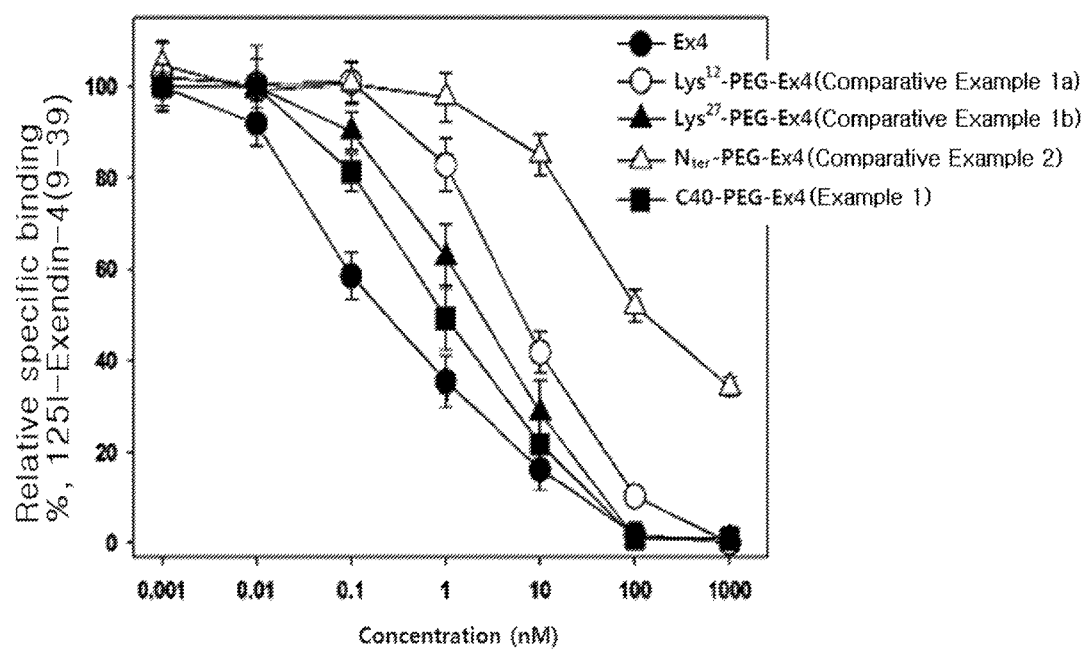
FIG. 10 is a view illustrating the affinity of a PEG bound exendin-4 analogue to a GLP-1 receptor according to an example of the present invention.

As a result of having measured affinity to a GLP-1 receptor of exendin-4 analogue PEGylated with polyethylene glycol or a derivative thereof according to the present invention, IC50 value was 1.04 nM, and this was confirmed to show 120 times more activity than compound of example 1 (Nter-PEG-Ex4) (IC50=121.78 nM) (refer to experimental example 1, Table 3 and FIG. 10).

Figure 11:
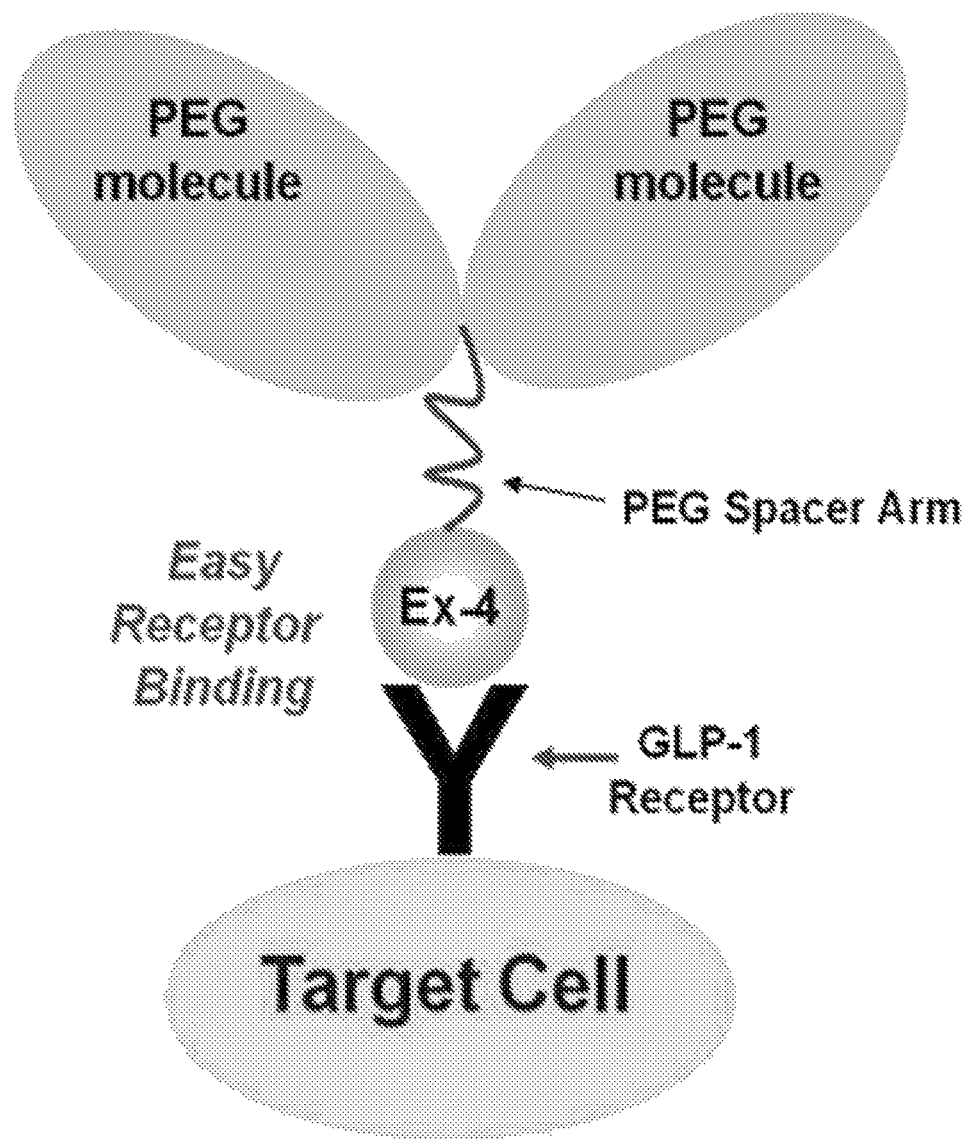
FIG. 11 is a schematic view illustrating PEG bound exendin-4 analogues of examples 4 and 5 of the present invention.

Also, for better understanding, a schematic diagram of the present invention's exendin-4 bound with a trimeric PEG at C40 site is shown in FIG. 11.

When the molecular weight of the bound PEG is 23K, PEG of 3 KD is used as a PEG spacer, and PEG having 10 KD molecular weight are bound to terminal of the 3 KD (example 4). Also, similar to this, when the molecular weight of the bound PEG is 50, PEG of 10 KD is used as a PEG spacer, and PEG having the molecular weight of 20 KD are bound to terminal of the 10 KD (example 5). At this time, as a result of having measured the required time of blood glucose level raising back to 8.35 mmol/L after having injected the exendin-4 of example 4 (C40-PEG23K-Ex4) and example 5 (C40-PEG50K-Ex4), low blood glucose level maintained from 45.5-56.1 hours after the administration of the medication (refer to experimental example 2, Table 4 and FIG. 12), which was confirmed to be more than twice of C40-PEG20K-Ex4 (23.2 hours) and control group (7.3 hours), enabling 7-8 times more stable maintenance of blood glucose level.

Therefore, the C40 site specific PEG bound exendin-4 compound according to the present invention can solve the drawback of quick excretion of medications due to the low molecular weight of existing exendin-4, has excellent affinity to the GLP-1 receptor, and has strong low blood glucose maintaining ability capable of maintaining blood glucose level up to 3-4 days after having administrated the medications, so it can be used beneficially for preventing or treating insulin hypersecretion related Type 1 diabetes, Type 2 diabetes and diseases related with diabetes complications.

When the composition of the present invention is used as medications, the pharmaceutical composition containing the exendin-4 analogue PEGylated with polyethylene glycol or a derivative thereof may be administrated after having formulated into various oral or non-oral administration forms as the following in case of clinical administration, but is not limited thereof.

For oral administration purposed formulation, for example, there are tablets, pellets, hard/soft capsules, liquids, suspensions, emulsifiers, syrups, granules, elixirs, troches, etc., and these formulations include diluents (example: lactose, dextrose, sucrose, mannitol, sorbitol, cellulose and/or glycine), slip modifiers (example: silica, talc, stearate and its magnesium or calcium salt and/or polyethylene glycol) in addition to the active ingredient. Tablets may also include binders such as magnesium aluminum silicate, starch paste, gelatin, methyl cellulose, sodium carboxymethyl cellulose and/or polyvinyl pyrrolidine, and may include disintegrating agents such as starch, agar, alginic acid or sodium salt thereof or boiling mixture and/or absorbents, coloring agents, flavoring agents and sweetening agents if needed.

The pharmaceutical composition containing the exendin-4 analogue PEGylated with polyethylene glycol or a derivative thereof may be non-orally administrated, and the administration is done by subcutaneous injection, intravenous injection, intramuscular injection or intrathoracic injection.

At this time, the exendin-4 analogue PEGylated with polyethylene glycol or a derivative thereof may be may be prepared into liquid or suspension by having mixed it with stabilizer or buffer in water to formulize it into non-orally administration purposed formulation, and this may be prepared into ampoule or vial unit administration form. The composition is sterilized and/or may include adjuvants such as antiseptics, stabilizers, hydrators or emulsify stimulators, osmotic pressure controlling purposed salts and/or buffers, and other substances beneficial for treatments, and may be formulated according to traditional methods of mixture, granulation or coating.

The human body dose of the pharmaceutical composition containing the exendin-4 analogue PEGylated with polyethylene glycol or a derivative thereof according to the present invention may vary depending on the age, body weight, gender, administration form, health status and level of disease of patients, and may be administrated via oral or non-oral route following decisions of doctors or pharmacists with preferably dose of 0.01 to 200 mg/kg/day.

MODE FOR CARRYING OUT THE INVENTION

The present invention will be explained in detail by examples and experimental examples hereafter.

The examples and experimental examples are only demonstrating the present invention, and the contents of the present invention are not limited thereof.

<Examples 1-5> C40 Site Specific PEG Bound Exendin-4 Production

To prepare C40 site specific PEG bound exendin-4, exendin-4-Cys in which cysteine is introduced into the C-terminal site (#40 site) was used (exendin-Cys, molecular weight: 4290.7, sequence: HGEGTFTSDLSKQMEEEAVR-LFIEWLKNGGPSSGAPPPSC (SEQ ID NO: 1)), and maleimide activated monomethoxy PEG (mPEG-MAL, MW: 5, 20 kDa (Linear type), 20 kDa (Branch type), 23, 50 kDa (Trimer type)) was purchased from Nippon Oil and Fats, NOF, Tokyo, and used.

Figure 4:
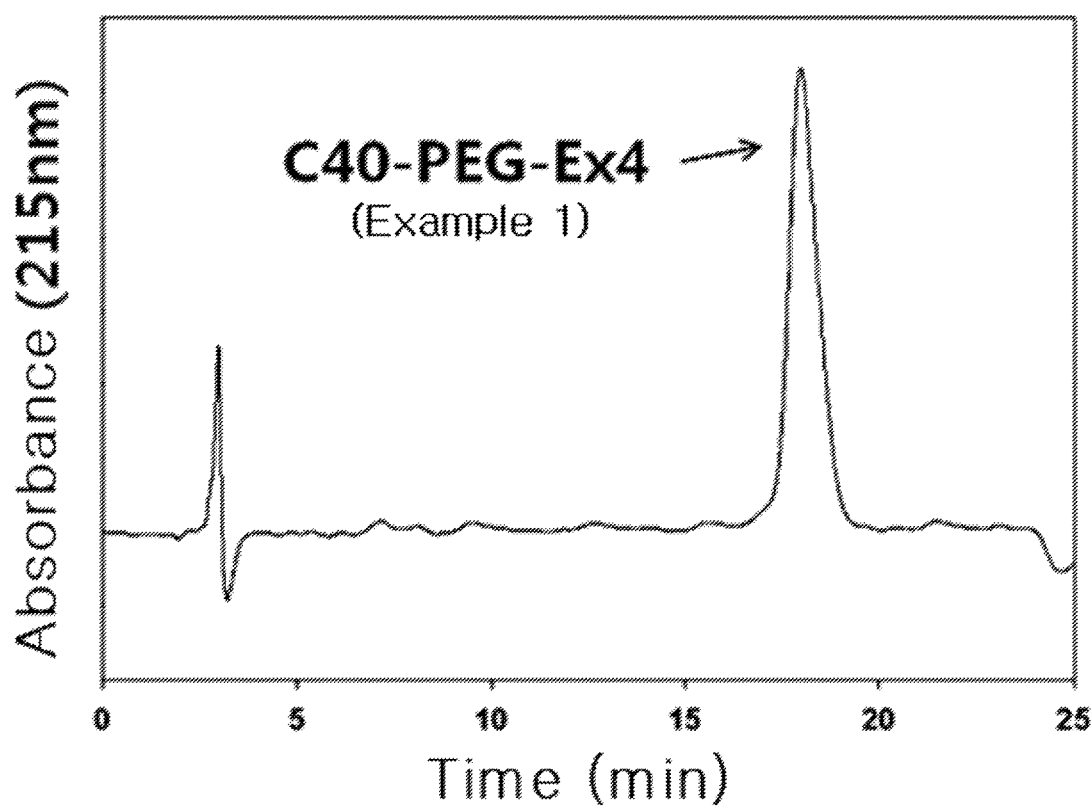
FIG. 4 is a view illustrating light absorbance of example 1 of the present invention.

To prepare C-terminal #40 site specific PEG bound exendin-4, exendin-4-Cys and mPEG-MAL (MW: 5, 20 (linear type), 20 (branch type), 23, 50 kDa) were completely dissolved in a mole ratio of 1:2 in a 20 mM phosphate buffer saline (pH 7.5) and were reacted for two hours at room temperature (refer to FIG. 1). After the reaction, the reacted solution was separated by a reversed phase chromatography with Capcell-pak RP-18 column (250×10 mm, 5 Shiseido, Japan) at a flow speed of 5.0 ml/min. The separation was monitored at 215 nm wavelength ultraviolet ray. The mobile phase was separated using a linear concentration gradient method (36-42% B over 30 min) for 0.1% TFA distilled water (mobile phase A) and 0.1% TFA acetonitrile (mobile phase B) (refer to FIG. 4).

The peaks separated by the method were collected separately, acetonitrile was removed using nitrogen gas, and the removed solution was concentrated using Centricon-10 (Mw cut off 3000, Millipore Corp., Billerica, Mass.). The prepared substance was stored at 4° C. and prepared by mixing 1 µl sample-matrix sample solution and 2 µl matrix solution, and the matrix solution was prepared by dissolving α-cyanohydroxycinnamic acid (α-CHCA) with water/CAN (50:50) solution containing 0.1% (v/v) TFA. The prepared 1 µl sample-matrix solution was put on a sample plate, dried at vacuum status and analyzed with size exclusion chromatography (SEC) and MALDI-TOF mass spectrometer, and C40 site specific PEG bonding reaction (C40-PEG-Ex4) was analyzed at 0, 20, 40, 60 and 80 minutes and was shown with chromatogram area ratio in comparison with the initial status of exendin-4 and C40-PEG-Ex4. The result is illustrated in Table 1 and FIG. 7.

TABLE 1

| | Reaction Time | Yield (%) |
|---|---|---|
| Example 1 C40-PEG$_{5K}$-Ex4 (linear) | 80 min. | 93% |
| Example 2 C40-PEG$_{20K}$-Ex4 (linear) | 80 min | 89% |
| Example 3 C40-PEG$_{20K}$-Ex4 (branch) | 80 min. | 91% |
| Example 4 C40-PEG$_{23K}$-Ex4 (trimer) | 80 min. | 90% |
| Example 5 C40-PEG$_{50K}$-Ex4 (trimer) | 80 min. | 85% |

Figure 7:
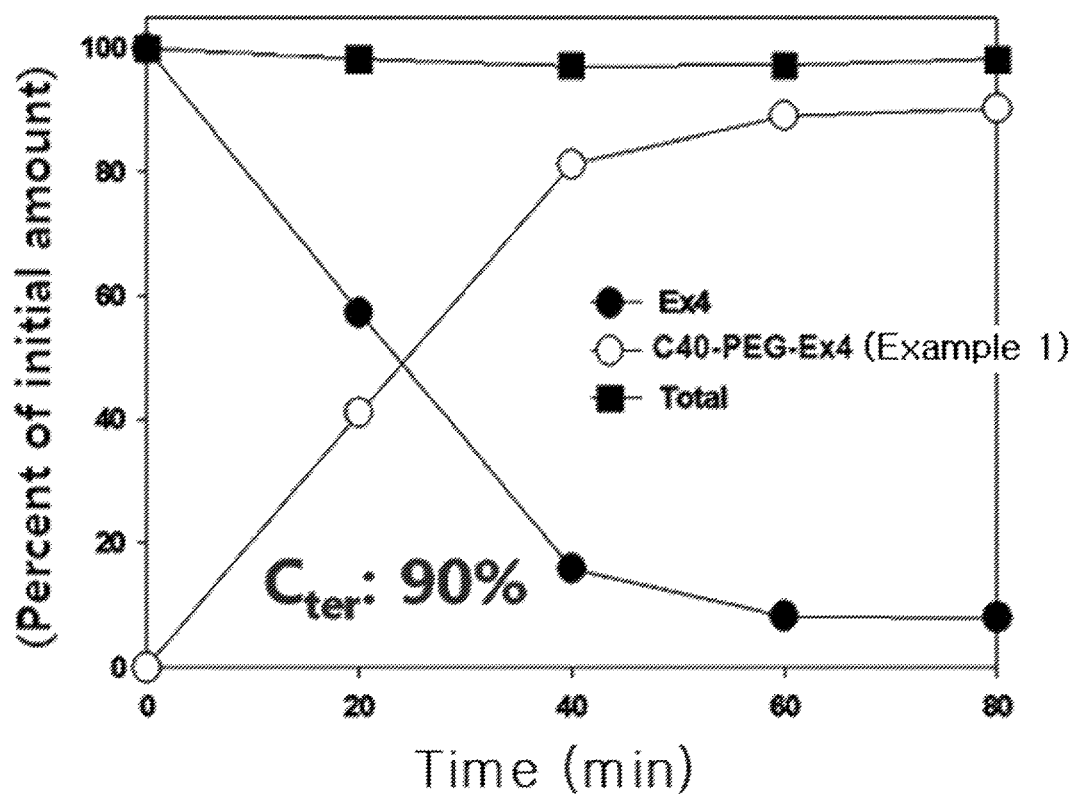
FIG. 7 is a view illustrating the production yield of example 1 of the present invention.

As shown in Table 1, the reaction time was 80 minutes in average, production being done with yield of over 90% average (refer to FIG. 7).

<Comparative Example 1> Production of Non-Specific PEG Bound Exendin-4

Figure 2:
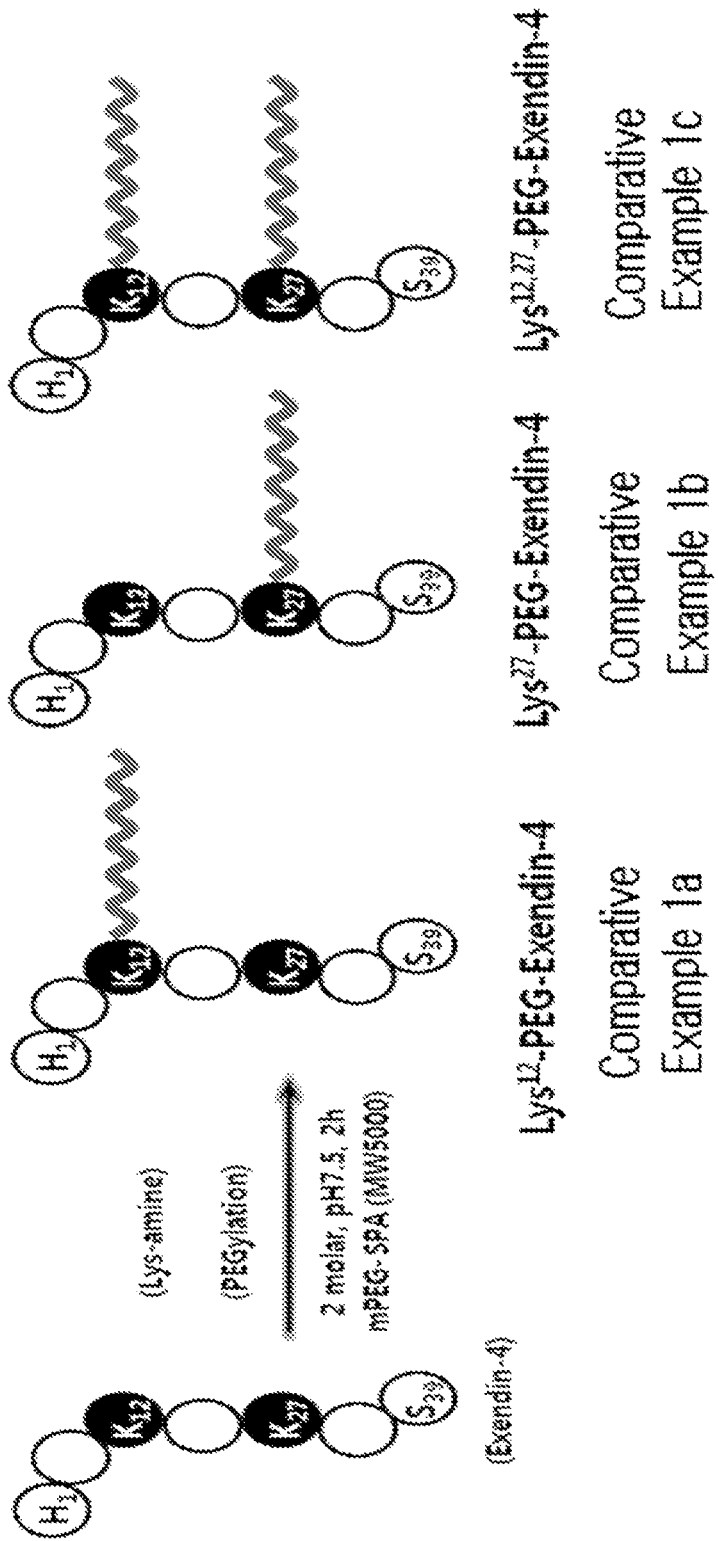
FIG. 2 is a schematic view illustrating PEGylation for lycine amine of exendin-4 of comparative example 1 of the present invention.
Figure 5:
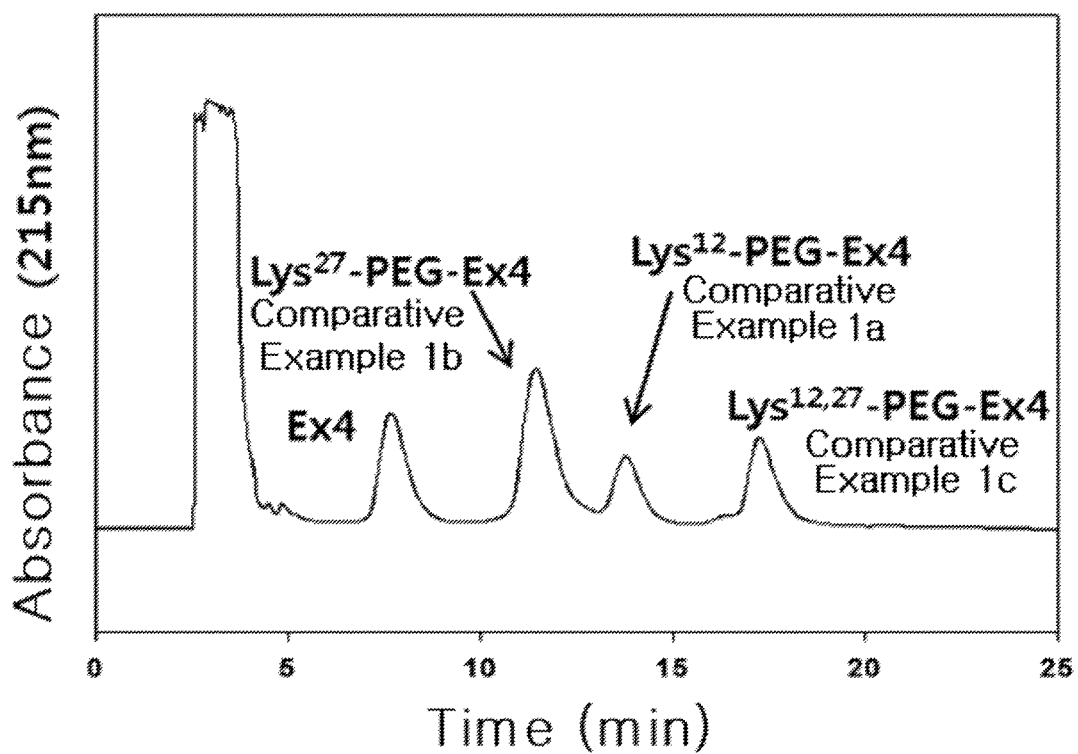
FIG. 5 is a view illustrating light absorbance of comparative examples 1a to 1c of the present invention.

A method equivalent to the example 1 except for using exendin-4 (molecular weight: 4186.6, sequence: HGEGTFTSDLSKQMEEEAVRLFIEWLKNGGPSSGAPPPS (SEQ ID NO: 2)) and succinimidyl activated monomethoxy PEG (mPEG-SPA, MW: 5, 20 kDa (Linear type)) instead of using cysteine introduced exendin-4-Cys and maleimide activated monomethoxy PEG, was performed to prepare non-specific PEG bound exendin-4 (refer to FIG. 2 and FIG. 5).

The succinimidyl activated monomethoxy PEG (mPEG-SPA) was purchased from Nippon Oil and Fats, NOF, Tokyo, and used.

TABLE 2

| Comparative example 1 | Reaction Time | Yield (%) |
|---|---|---|
| Comparative example 1a Lys$^{12}$-PEG$_{20K}$-Ex4 | 80 min. | 20% |
| Comparative example 1b Lys$^{27}$-PEG$_{20K}$-Ex4 | 80 min. | 31% |
| Comparative example 1c Lys$^{12,27}$-PEG$_{20K}$-Ex4 | 80 min. | 25% |

Figure 8:
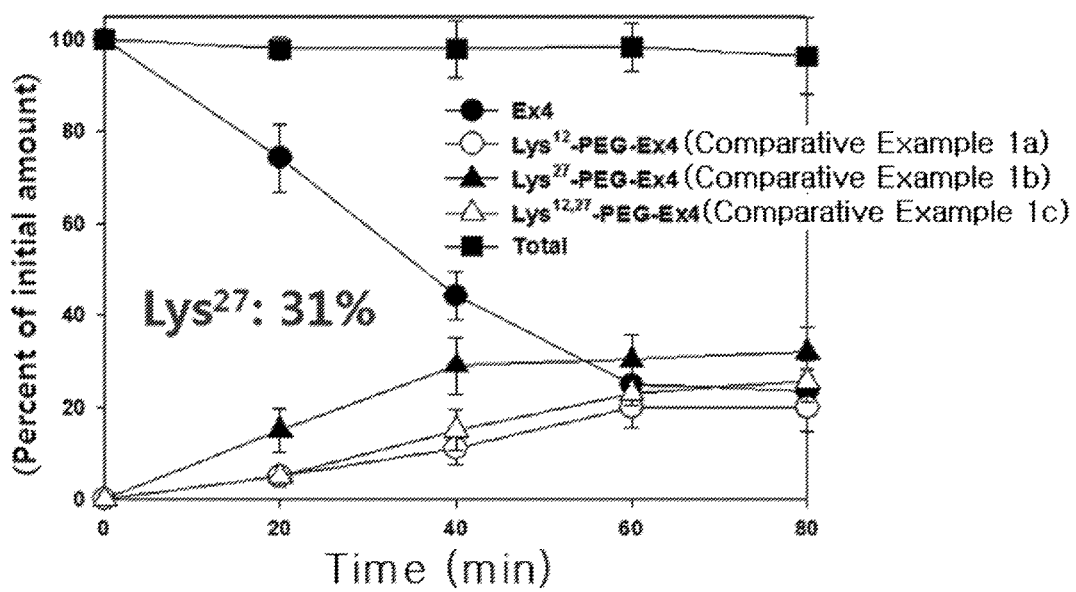
FIG. 8 is a drawing illustrating product yield of comparative examples 1a to 1c of the present invention.

As shown in Table 2, the reaction time of non-specific primary amine PEG binding reaction was 80 minutes in average, average yield being 20% for Comparative example 1a (Lys$^{12}$-PEG$_{20K}$-Ex4) and 31% for Comparative example 1b (Lys$^{27}$-PEG$_{20K}$-Ex4) (refer to FIG. 8).

<Comparative Example 2> N-Terminal Specific PEG Bound Exendin-4 Production

Figure 3:
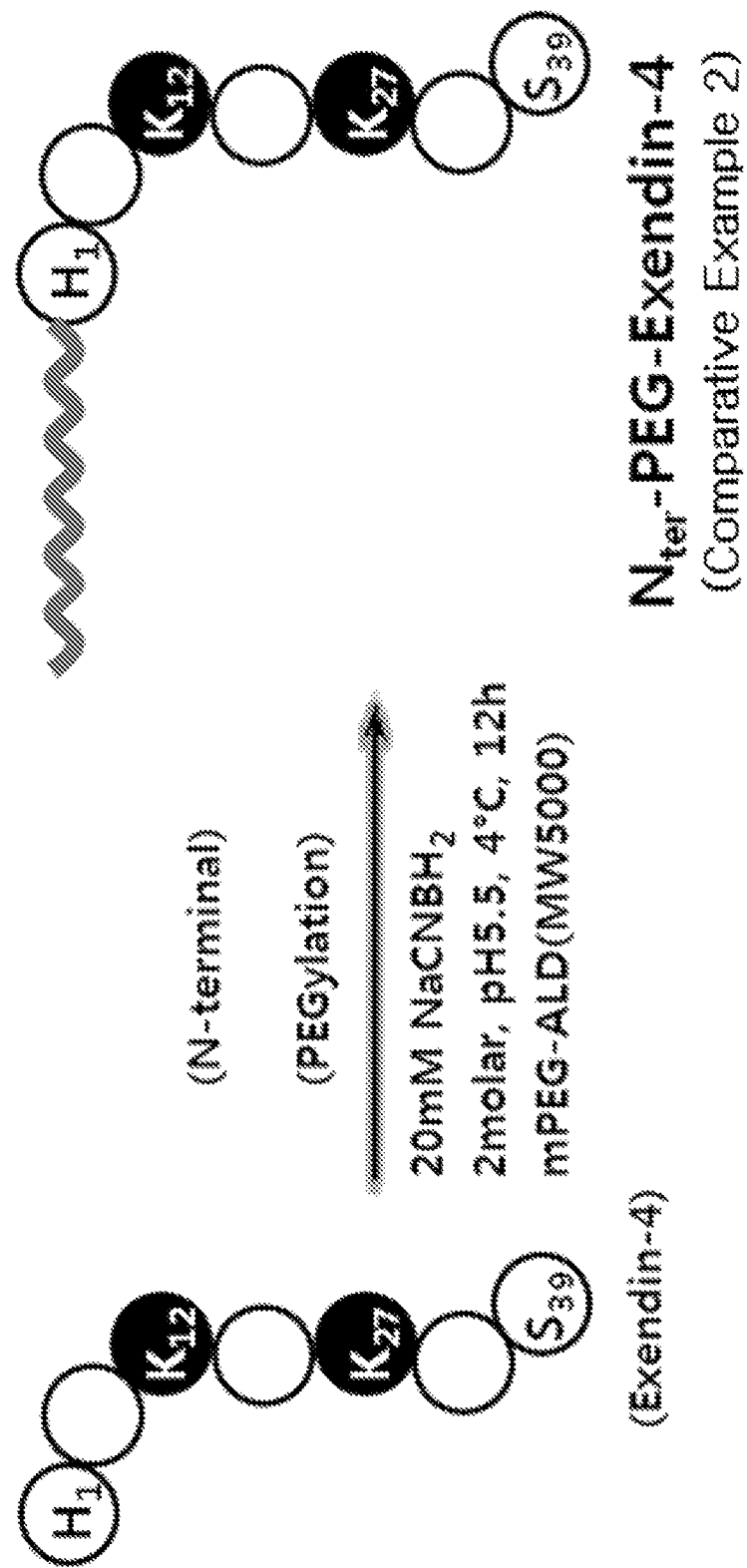
FIG. 3 is a schematic view illustrating PEGylation for N-terminal of exendin-4 of comparative example 2 of the present invention.
Figure 6:
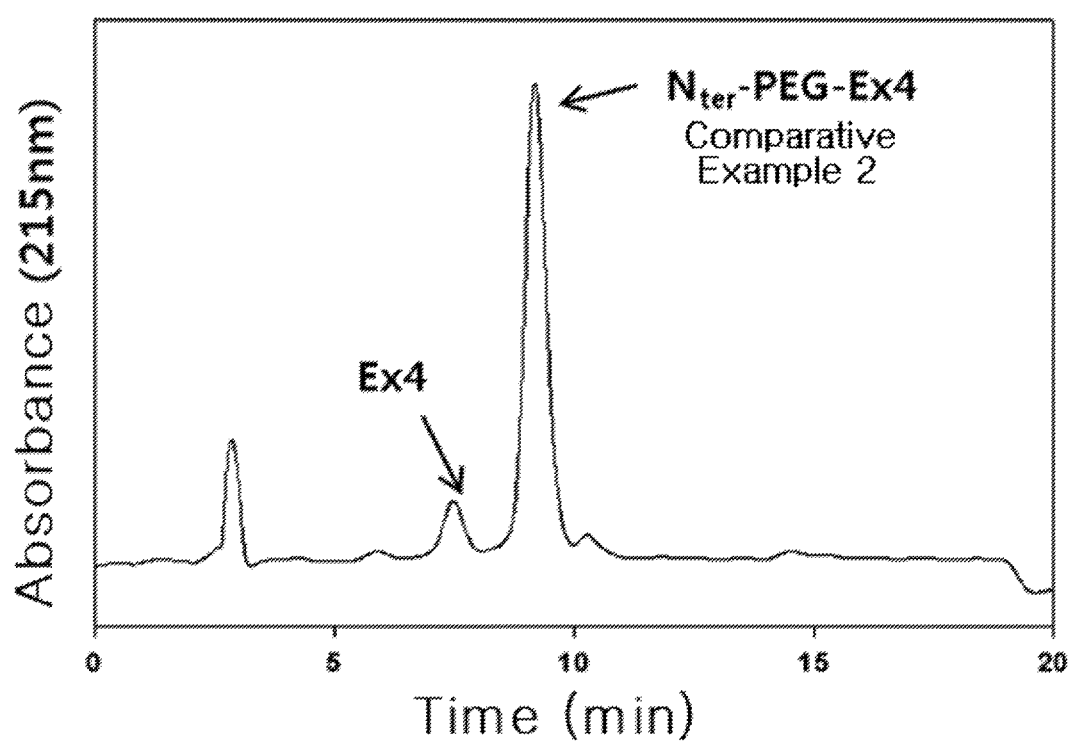
FIG. 6 is a view illustrating light absorbance of comparative example 2 of the present invention.

A method equivalent to the example 1 except for using exendin-4 (molecular weight: 4186.6, sequence: HGEGTFTSDLSKQMEEEAVRLFIEWLKNGGPSSGAPPPS (SEQ ID NO: 2)) and monomethoxy PEG-aldehyde (mPEG-ALD, MW: 5 kDa (linear)) instead of using cysteine introduced exendin-4-Cys and maleimide activated monomethoxy PEG, was performed to prepare non-specific PEG bound exendin-4 (refer to FIG. 3 and FIG. 6).

The monomethoxy PEG-aldehyde was purchased from Nippon Oil and Fats, NOF, Tokyo and used.

Figure 9:
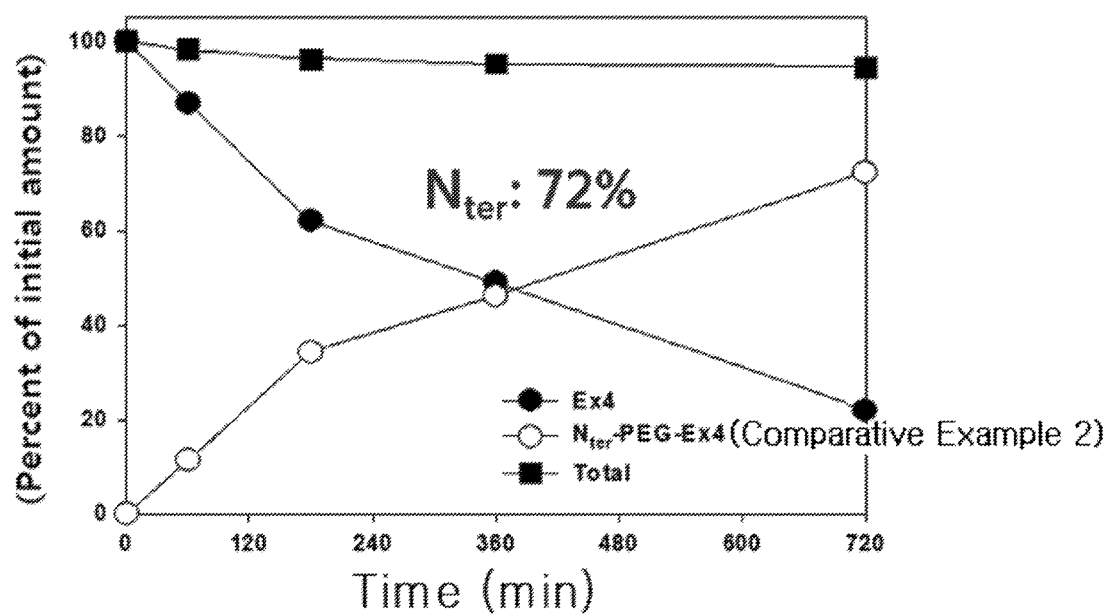
FIG. 9 is a view illustrating the production yield of comparative example 2 of the present invention.

As a result, the reaction time of N-terminal specific PEG binding reaction (N$_{ter}$-PEG$_{5K}$-Ex4) was 720 minutes, with average yield of 72% (refer to FIG. 9).

<Experimental Example 1> Analysis of RIN-m5F Cell Receptor Binding Affinity of PEG Bound Exendin-4 Analogue The following experiment was performed to perform GLP-1 receptor (GLP-1R) affinity of PEG bound exendin-4 analogues of Example 1 (C40-PEG$_{5K}$-Ex4), Comparative example 1a (Lys$^{12}$-PEG$_{5K}$-Ex4), Comparative example 1b (Lys$^{27}$-PEG$_{5K}$-Ex4) and Comparative example 2 (N$_{ter}$-PEG$_{5K}$-Ex4) prepared in Example 1, Comparative example 1 and 2.

Islet cells (RIN-m5F, ATCC, Manassas, Va.) expressing vast quantity of GLP-1 receptor (GLP-1R) were inoculated in 12-wells plates. It was washed twice with binding buffer (120 mM NaCl, 1.2 mM MgSO$_4$, 13 mM sodium acetate, 5 mM KCl, 1.2 g/l Tris, 2 g/l bovine serum albumin, 1.8 g/l glucose, pH 7.6) after 48 hours and unmarked PEG bound exendin-4 analogue (final concentration range: 0.001-1000 nM) and exendin-4 marked with 30 pM concentration I-125 (9-39, PerkinElmer, Boston, Mass.) were treated simultaneously. Thorough washing was done with PBS including 1 mg/mg bovine serum albumin after two hours. Finally the cells were thoroughly degraded for 15 minutes using cell lysis buffer (0.5 N NaOH with 1% SDS), and the radiation level of I-125 was measured using a gamma counter (GMI, Inc., Ramsey, Minn.). The result is illustrated in Table 3 and FIG. 10.

TABLE 3

| | IC$_{50}$ (nM) |
|---|---|
| Example 1 (C40-PEG$_{5K}$-Ex4) | 1.04 nM |
| Comparative example 1a (Lys$^{12}$-PEG$_{5K}$-Ex4) | 6.45 nM |
| Comparative example 1b (Lys$^{27}$-PEG$_{5K}$-Ex4) | 2.42 nM |
| Comparative example 2 (N$_{ter}$-PEG$_{5K}$-Ex4) | 121.78 nM |
| Control group (exendin-4) | 0.23 nM |

As shown in Table 3, IC$_{50}$ of Example 1 (C40-PEG$_{5K}$-Ex4) according to the present invention was confirmed to be 1.04 nM after the affinity for GLP-1 receptor was measured. It was confirmed that it shows activity twice better than Comparative example 1b (Lys$^{27}$-PEG$_{5K}$-Ex4) (IC$_{50}$ value=2.42 nM), and 6 times better than Comparative example 1a (Lys$^{12}$-PEG$_{5K}$-Ex4) (IC$_{50}$ value=6.45 nM). Also, it was confirmed that Example 1 (C40-PEG$_{5K}$-Ex4) according to the present invention shows activity 120 times better than Comparative example 2 (N$_{ter}$-PEG$_{5K}$-Ex4) (IC$_{50}$ value=121.78 nM).

Therefore, C40 site specific PEG bound exendin-4 composition according to the present invention not only can solve the weakness of quick excretion of medications due to low molecular weight of exendin-4, but also can be used beneficially as a diabetes medication since GLP-1 receptor affinity shows similar biological activity as exendin-4 (refer to FIG. 10).

<Experimental Example 2> Evaluation of Low Blood Glucose Sustainability in Non-Fasting Type 2 Diabetic Mice The following experiment was performed to evaluate low blood glucose sustainability of C40 site specific PEG bound exendin-4 composition according to the present invention in Type 2 diabetic mice.

Type 2 diabetic C57BL/6 db/db mice (male, 4-5 weeks old, Central Lab. Animal Inc.) were used, and animals were exposed to light at 12 hours cycle and were grown after having stabilized two week by allowing free intake of foods and water. The experimental animals were managed following the guideline of National Institute of Health (NIH) and authorized by Institutional Animal Care and Use Committee of Sungkyunkwan University, and the experiment was performed humanely.

C40-PEG$_{5K}$-Ex4 (linear), C40-PEG$_{20K}$-Ex4 (linear), C40-PEG$_{20K}$-Ex4 (branch), C40-PEG$_{23K}$-Ex4 (trimer) and C40-PEG$_{50K}$-Ex4 (trimer) prepared from the Example 1 to 5 and Lys$^{27}$-PEG$_{20K}$-Ex4 prepared in Comparative example 1b were intraperitoneally injected with 25 nmol/kg dose to male db/db mice (6-7 weeks old), blood was collected from tail vein of mice following the float time: 0, 0.5, 1, 2, 3, 4, 6, 8, 12, 24, 36, 48, 60, 72, 96 hours and blood glucose concentration was measured with ACCU-CHEK Sensor (Roche Diagnostics Corp., USA). Afterwards, the low blood glucose sustaining time (blood glucose level<8.35 mmol/l (150 mg/dL)) was additionally measured and shown in Table 4 and FIG. 12. In the present experiment, exendin-4 was used as the control group.

present invention as an active ingredient, and the present invention is not limited thereof.

<Formulation Example 1> Production of Powders

C40 site specific PEG bound exendin-4 analogue 2 g
Lactose 1 g
The ingredients were mixed and stuffed in sealed packages to prepare powders.

<Formulation Example 2> Production of Tablets

C40 site specific PEG bound exendin-4 analogue 100 mg
Corn starch 100 mg
Lactose 100 mg
Magnesium stearate 2 mg
The ingredients were mixed and compressed according to general preparation methods for tablets to prepare tablets.

TABLE 4

| | Blood glucose level (mmol/l) (average) | | | | | | | |
|---|---|---|---|---|---|---|---|---|
| | C40-PEG-Ex4 | | | | | Comparative Example 1b (Lys$^{27}$-PEG$_{20K}$-Ex4) | Control group (Ex-4) | Untreated group |
| Time (h) | Example 1 (PEG$_{5K}$) | Example 2 (PEG$_{20K}$) | Example 3 (PEG$_{20K}$) | Example 4 (PEG$_{23K}$) | Example 5 (PEG$_{50K}$) | | | |
| 0 | 23.38 | 24.28 | 24.44 | 24.22 | 24.56 | 24.13 | 22.61 | 24.23 |
| 0.5 | 7.62 | 7.96 | 7.86 | 7.97 | 7.63 | 7.97 | 6.95 | 24.21 |
| 1 | 7.36 | 6.13 | 6.89 | 6.99 | 6.25 | 6.56 | 6.41 | 23.44 |
| 2 | 5.09 | 5.29 | 5.04 | 4.96 | 5.45 | 5.24 | 5.80 | 24.58 |
| 3 | 4.46 | 4.18 | 4.15 | 4.11 | 4.64 | 4.22 | 5.85 | 22.96 |
| 4 | 4.93 | 4.34 | 4.66 | 4.54 | 4.23 | 4.29 | 8.02 | 24.54 |
| 6 | 5.73 | 4.9 | 4.67 | 4.87 | 4.26 | 4.85 | 10.69 | 23.43 |
| 8 | 9.04 | 4.57 | 5.11 | 4.66 | 4.69 | 5.13 | 16.01 | 24.94 |
| 12 | 16.2 | 5.86 | 7.89 | 4.9 | 4.87 | 5.40 | 23.89 | 22.47 |
| 24 | 21.1 | 8.54 | 15.09 | 5.52 | 5.11 | 12.98 | — | 24.42 |
| 36 | — | 11.47 | 20.14 | 8.08 | 6.31 | 17.34 | — | 23.92 |
| 48 | — | 15.34 | 24.21 | 8.66 | 7.26 | 20.45 | — | 22.66 |
| 60 | — | 20.45 | 23.76 | 11.34 | 8.87 | 23.02 | — | 23.41 |
| 72 | — | 23.02 | — | 14.12 | 13.49 | — | — | 22.26 |
| 96 | — | — | — | 18.79 | 17.07 | — | — | 24.51 |
| 120 | — | — | — | 24.53 | 23.02 | — | — | 23.75 |

Figure 12:
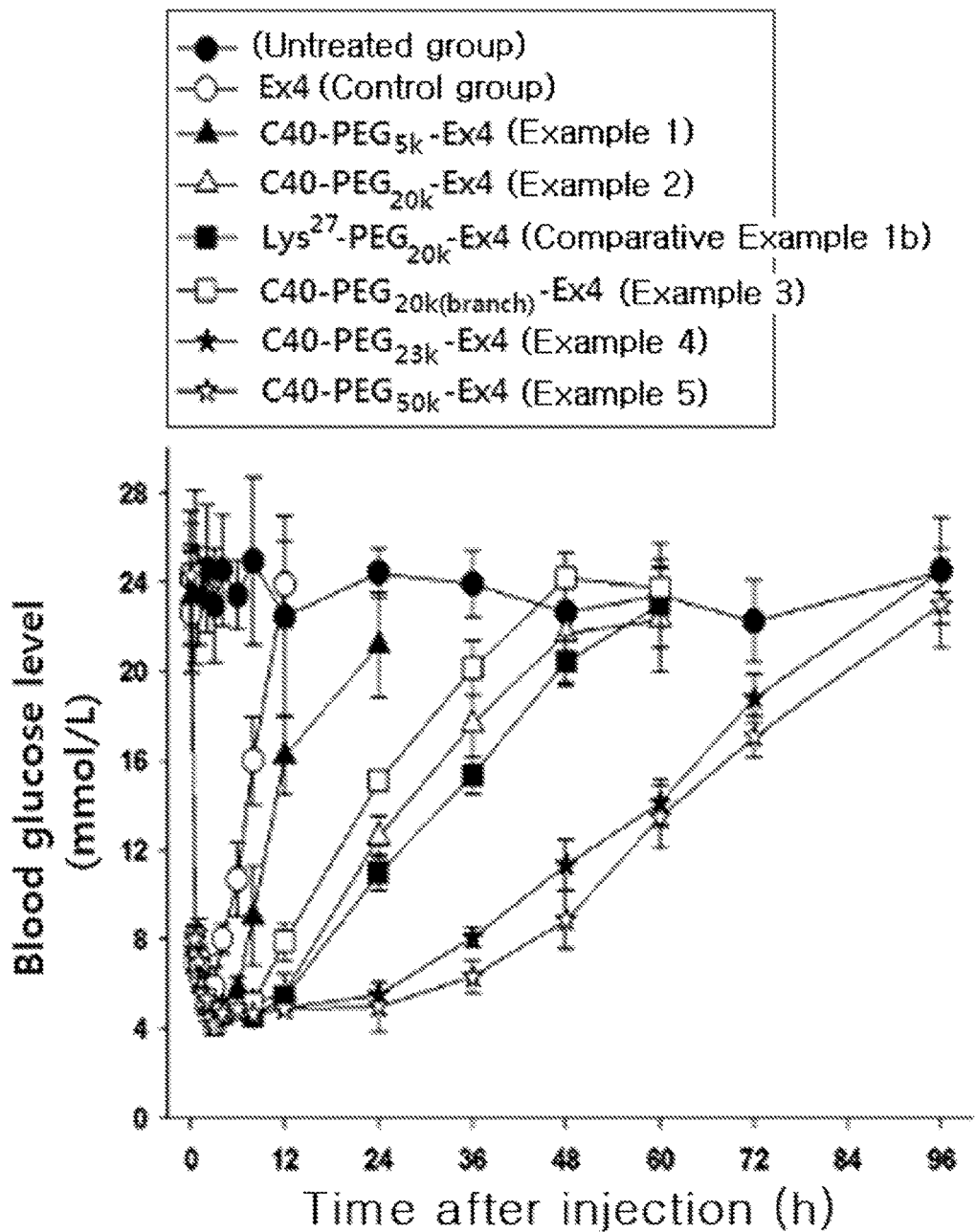
FIG. 12 is a view illustrating blood glucose level for diabetic mice administrated with a PEG bound exendin-4 analogue according to an example of the present invention.

As shown in Table 4, the time required for blood glucose level of C40 site specific PEG bound exendin-4 of Examples 1 to 5 according to the present invention increasing back to 8.35 mmol/l was confirmed to be longer than exendin-4 (7.3 hours), and especially for Example 4 (C40-PEG$_{23K}$-Ex4) and Example 5 (C40-PEG$_{50K}$-Ex4) which were introduced with trimer PEG, the low blood glucose level sustained for 45.5 hours and 56.1 hours, respectively (refer to FIG. 12).

Therefore, C40 site specific PEG bound exendin-4 composition according to the present invention can be used beneficially as a diabetes medication by having solved the weakness of quick excretion of medications due to low molecular weight of exendin-4 and consequently sustaining blood glucose level 7-8 times more stable than the Comparative examples.

Meanwhile, C40 site specific PEG bound exendin-4 analogue according to the present invention can be formulated into various forms following purposes. The following is an illustration of few formulation methods that include C40 site specific PEG bound exendin-4 analogue according to the <Formulation Example 3> Production of Capsule C40 site specific PEG bound exendin-4 analogue 100 mg
Corn starch 100 mg
Lactose 100 mg
Magnesium stearate 2 mg
The ingredients were mixed and stuffed in gelatin capsules according to general preparation methods for capsules to prepare capsules.

<Formulation Example 4> Production of Injections

C40 site specific PEG bound exendin-4 analogue 100 mg
Mannitol 180 mg
Na$_2$HPO$_4$.2H$_2$O 26 mg
Distilled water 2974 mg
The ingredients were included with the given quantity according to general preparation methods for injections to prepare injections.

INDUSTRIAL APPLICABILITY

According to the present invention, by performing selective PEGylation, the yield of an exendin-4 analogue in which a cysteine (Cys) is introduced into #40 site of the C-terminal and is PEGylated with polyethylene glycol (PEG) or a derivative thereof, can be increased and the treatment effect of medications can be increased, and thus the exendin-4 analogue can be beneficially used as a composition for prevention or treatment of diseases caused by insulin hypersecretion.

We claim:

1. An exendin-4 analogue comprising SEQ ID NO:2 and a cysteine (Cys) added to the c-terminal end of SEQ ID NO:2 and PEGylated with a trimer of polyethylene glycol (PEG) or a methoxy-activated derivative of PEG, wherein the trimer comprises a polyethylene glycol or a methoxy-activated derivative thereof spacer, wherein the spacer is connected to the terminal cysteine, and wherein the spacer has a molecular weight between 3 kDa and 10 kDa, and the trimer of PEG, or the methoxy-activated derivative of PEG, comprising the spacer has a molecular weight greater than 20 and up to 50 kDa.

2. The exendin-4 analogue of claim 1, wherein the trimer comprises a branched derivative of methoxypolyethylene glycol succinimidylpropionate, methoxypolyethylene glycol N-hydroxysuccinimide, methoxypolyethylene glycol propionaldehyde, or methoxypolyethylene glycol maleimide.

3. The exendin-4 analogue of claim 1, wherein the methoxy-activated polyethylene glycol derivative is methoxypolyethylene glycol maleimide.

4. A pharmaceutical composition for treating type 1 or type 2 diabetes, comprising the exendin-4 analogue of claim 1 as an active ingredient.

5. The pharmaceutical composition of claim 4 for injection.

6. The exendin-4 analogue of claim 1, wherein the cysteine is introduced as amino acid 40.

7. A method of preparing the exendin-4 analogue of claim 1, the method comprising reacting the added cysteine in the exendin-4 with the trimer of PEG or methoxy-activated derivative thereof.

8. The method of claim 7, wherein the reaction mole ratio of the exendin-4 having the added cysteine and the trimer of polyethylene glycol or the methoxy-activated derivative thereof is 1:1, 1:2, or 1:3.

9. The method of claim 7, further comprising dissolving the exendin-4 in which a cysteine is added to the C-terminal end and the trimer of polyethylene glycol or a methoxy-activated derivative thereof in a phosphate buffer saline solution; and reacting the dissolved ingredients at room temperature.

10. The method of claim 9, wherein the phosphate buffer saline has a pH between 7.2 and 7.8.

11. The method of claim 7, wherein the trimer is trimeric methoxypolyethylene glycol maleimide.

12. The method of claim 10, wherein the cysteine is introduced as amino acid 40.

13. A method of treating diabetes in a patient in need thereof comprising administering a first dose of a composition comprising a therapeutically effective amount of the exendin-4 analogue of claim 1.

14. The method of claim 13, wherein the patient has Type 1 diabetes or Type 2 diabetes.

15. The method of claim 13, wherein the trimer is trimeric methoxypolyethylene glycol maleimide.

16. The method of claim 13, further comprising administering a second dose at a period of time greater than three days after administration of the first dose.

17. The method of claim 13, wherein the composition is effective for a period of time greater than 24 hours after administration of the first dose.

18. The method of claim 13, wherein the composition is effective for a period of time greater than 3 days after administration of the first dose.

19. The method of claim 13, wherein the composition is administered weekly.

20. The method of claim 13, wherein the cysteine is introduced as amino acid 40.

* * * * *

UNITED STATES PATENT AND TRADEMARK OFFICE
CERTIFICATE OF CORRECTION

| | |
|---|---|
| PATENT NO. | : 10,406,230 B2 |
| APPLICATION NO. | : 15/413029 |
| DATED | : September 10, 2019 |
| INVENTOR(S) | : Sung Kwon Lee et al. |

It is certified that error appears in the above-identified patent and that said Letters Patent is hereby corrected as shown below:

In the Specification

Column 2, Line 7, replace "primary amine site" with --a primary amine site--.
Column 2, Line 8, replace "different amino acid" with --a different amino acid--.
Column 2, Line 33, replace "reduces" with --reduce--.
Column 2, Line 33, replace "suppresses" with --suppress--.
Column 2, Line 38, replace "is" with --has--.
Column 3, Lines 23-24, replace "treatment effect" with --the treatment effect--.
Column 3, Line 35, replace "lycine" with --lysine--.
Column 3, Line 46, replace "production yield" with --the product yield--.
Column 3, Line 50, replace "production yield" with --the product yield--.
Column 4, Lines 12-13, replace "succinimidylpropionate" with --succinimidyl propionate--.
Column 4, Line 34, replace "in a phosphate buffer saline solution in a mole" with --in a mole--.
Column 4, Line 37, replace "perform" with --performing--.
Column 4, Line 46, replace "mass spectroscope" with --mass spectroscopy--.
Column 4, Line 66, replace "IC50 value" with --the IC50 value--.
Column 4, Line 67, replace "120 times more activity" with --a 120 times more activity--.
Column 5, Line 61, replace "may be may be" with --may be--.
Column 5, Line 63, replace "stabilizer or buffer" with --a stabilizer or a buffer--.
Column 5, Line 63, replace "non-orally" with --a non-orally--.
Column 5, Line 67, replace "emulsify stimulators" with --emulsifying stimulators--.
Column 6, Line 13, replace "preferably dose" with --a preferable dose--.
Column 6, Lines 57-58, replace "α-cyanohydroxycinnamic acid" with --α-cyano-hydroxycinnamic acid--.
Column 6, Line 58, replace "water/CAN" with --water/ACN--.
Column 7, Line 48, replace "average yield" with --an average yield--.
Column 7, Line 67, replace "average yield" with --an average yield--.
Column 8, Line 14, replace "12-wells plates" with --12-well plates--.
Column 8, Line 14, replace "binding buffer" with --a binding buffer--.
Column 8, Line 43, replace "shows activity" with --shows an activity--.

Signed and Sealed this
Seventeenth Day of March, 2020

Andrei Iancu
*Director of the United States Patent and Trademark Office*

CERTIFICATE OF CORRECTION (continued)
U.S. Pat. No. 10,406,230 B2

Column 8, Line 48, replace "shows activity" with --shows an activity--.
Column 8, Line 54, replace "low molecular weight" with --the low molecular weight--.
Column 9, Line 2, replace "two week" with --for two weeks--.
Column 9, Line 10, replace "the Example" with --Examples--.
Column 9, Line 66, replace "few formulation methods" with --a few formulation methods--.
Column 10, Line 47, replace "Production of Capsule" with --Production of Capsules--.

In the Claims

Claim 1, Column 11, Line 50, replace "c-terminal" with --C-terminal--.
Claim 2, Column 11, Line 62, replace "succinimidylpropionate" with --succinimidyl propionate--.
Claim 7, Column 12, Line 10, replace "methoxy-activated" with --the methoxy-activated--.
Claim 10, Column 12, Lines 58-59, replace "phosphate buffer saline" with --phosphate buffer saline solution--.